United States Patent [19]

Hubmann et al.

[11] 4,217,912
[45] Aug. 19, 1980

[54] DEVICE FOR DETERMINATION OF THE MECHANICAL CHARACTERISTIC FREQUENCY OF BLOOD VESSELS, TENDONS, BONES OR SIMILAR ORGANS IN A BODY

[75] Inventors: Max Hubmann, Erlangen; Erich Lang, Spardorf; Franz Menke, Neckargemünd, all of Fed. Rep. of Germany

[73] Assignee: Industrie-Automation GmbH & Co., Heidelberg, Fed. Rep. of Germany

[21] Appl. No.: 941,968

[22] Filed: Sep. 13, 1978

[30] Foreign Application Priority Data

Sep. 14, 1977 [DE] Fed. Rep. of Germany ....... 2741338

[51] Int. Cl.³ .............................................. A61B 5/00
[52] U.S. Cl. .................................... 128/774; 128/739; 73/574
[58] Field of Search ...................... 128/774, 739, 782; 73/570, 574, 576

[56] References Cited

U.S. PATENT DOCUMENTS 2,742,035   4/1956   Hancock et al. ..................... 128/739

OTHER PUBLICATIONS

23rd Annual Conference on Engineering in Medicine and Biology—Washington, D.C., by Kronick et al., 11/15/70.

*Primary Examiner*—Willis Little
*Attorney, Agent, or Firm*—Martin A. Farber

[57] ABSTRACT

A transmitter for mechanical oscillations of variable frequency and an oscillation pickup for determination of the mechanical characteristic frequency of blood vessels, tendons, bones or similar organs in a body, by which these organs act as coupling members between the transmitter and the oscillation pickup. The transmission means from the transmitter to the body and from the body to the oscillation pickup are accommodated inside of a common support tube. One end of the support tube is rigidly connected with the support frame, in which support frame, the transmitter and the oscillation pickup are installed mutually decoupled, with even amplifiers or the like being installed, connected after the oscillation pickup, if necessary under the circumstances. The other end of the support tube is able to be set on the body.

9 Claims, 4 Drawing Figures

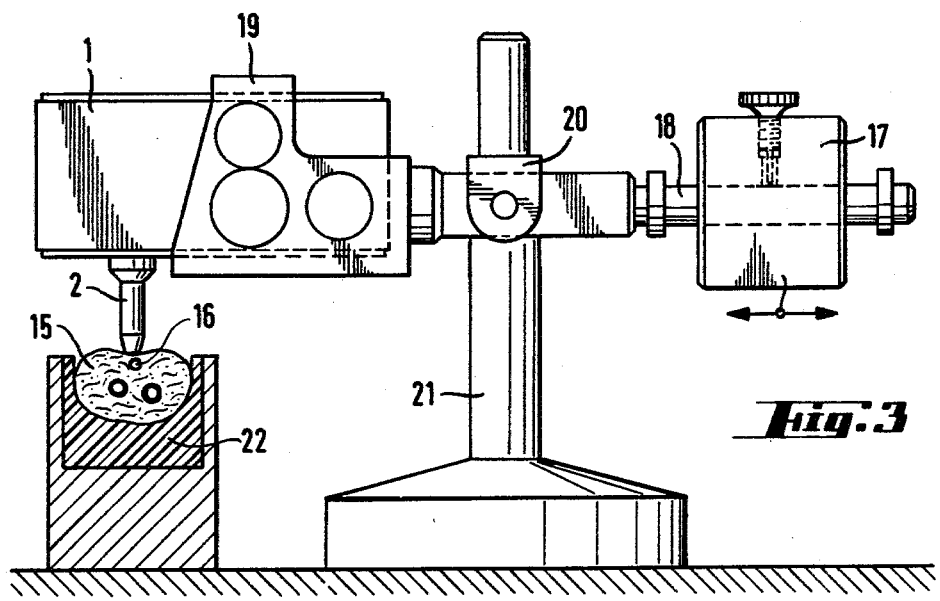
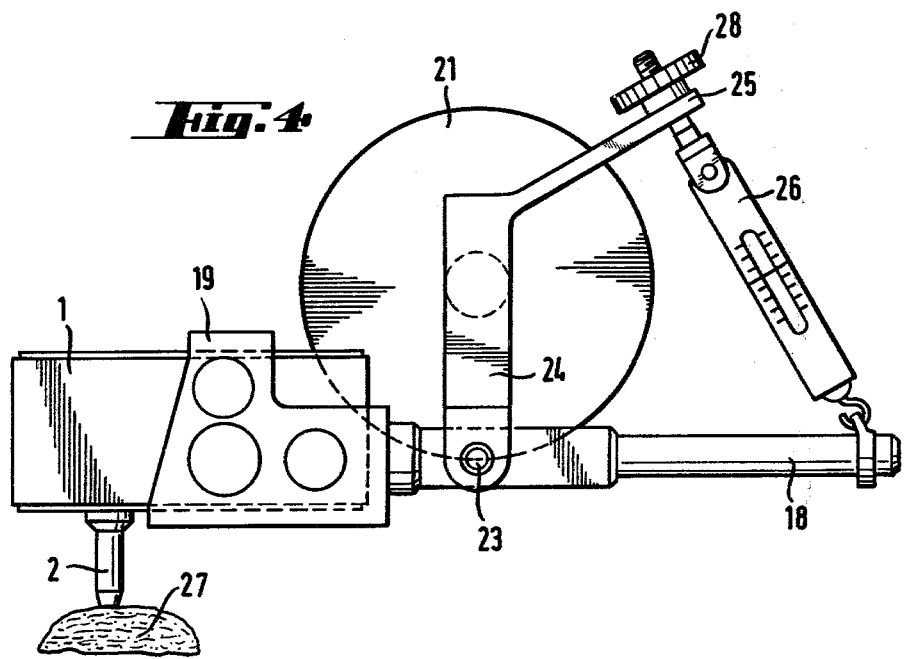

DEVICE FOR DETERMINATION OF THE MECHANICAL CHARACTERISTIC FREQUENCY OF BLOOD VESSELS, TENDONS, BONES OR SIMILAR ORGANS IN A BODY

The invention relates to a device comprising a transmitter for mechanical oscillations of variable frequency and an oscillation pickup for determination of the mechanical characteristic frequency of blood vessels, tendons, bones or similar organs in a body, by which these organs act as coupling members between the transmitter and the oscillation pickup.

Such devices serve diagnostic purposes, particularly for the purpose of determining deviations from the normal characteristic frequency or the time change of organs, e.g., of the radial artery and in this manner to recognize changes conditioned by old age or because of sickness.

Devices for determination of such characteristic frequencies are known, by which, above the part of the body in which the organ is located, the characteristic frequency of which is to be measured, there is arranged a transmitter for the mechanical vibrations or oscillations; the oscillations of the transmitter, which are variable in frequency, are mechanically transmitted to the relevant body part. An oscillation pickup is arranged separately from the transmitter. Maxima of the output voltage with certain frequencies indicates the characteristic frequency of the coupling member between the transmitter and the oscillation pickup.

These known devices have the disadvantage that their adjustment is very cumbersome and it is very difficult to achieve reproducable measuring results. Particularly this causes disadvantages when, the time variation, e.g., by aging, is to be followed, by measurements in more or less large time periods.

The invention is based on the object to make a device which is simple to adjust, easy to adapt to different circumstances and thereby provides good reproducable results.

In accordance with the invention this task is solved in the manner that the device comprises a transmitter for mechanical oscillations of variable frequency and an oscillation or vibration pickup. The transmission means from the transmitter to the body and from the body to the oscillation pickup are accommodated inside of a common support tube. One end of the support tube is rigidly connected with the support frame, in which support frame, the transmitter and the oscillation pickup are installed mutually decoupled, with even amplifiers A or the like being installed, connected after the oscillation pickup, if necessary under the circumstances. The other end of the support tube is able to be set on the body.

In order to improve the reproducability of the measurements, suitable means are provided for adjustment of the application pressure.

In the drawing, embodiment examples of the device according to the invention are illustrated. It shows:

FIG. 3 is the front view of the device for the mounting of the support tube to the body from above and from below, respectively, FIG. 4 is a plan view of an arrangement of the device for the lateral placement on the body.

Figure 1:
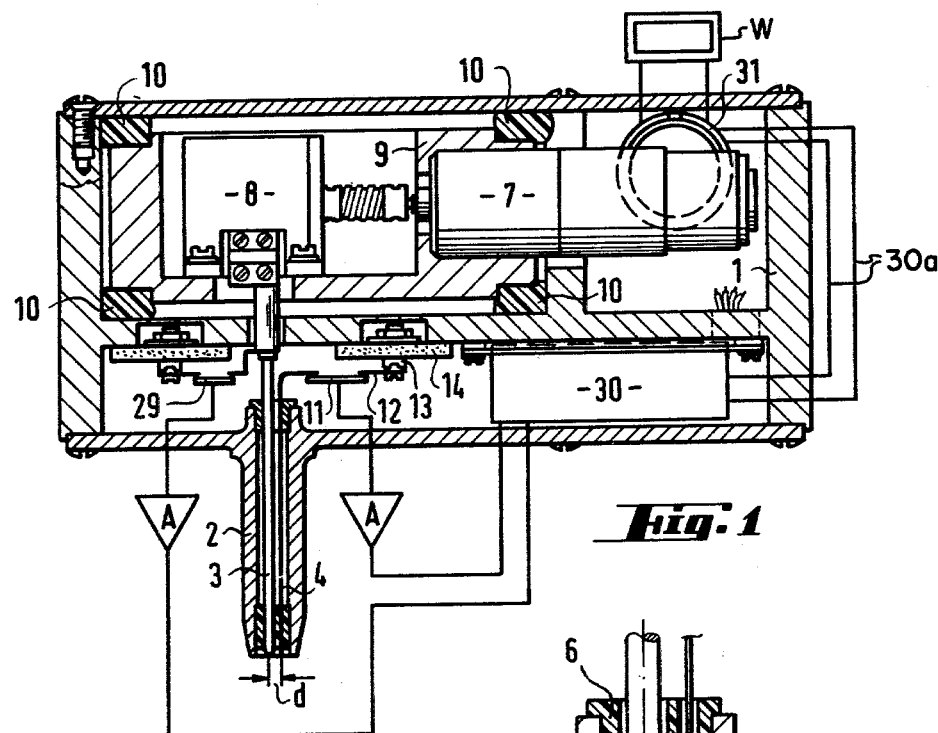
FIG. 1 is a section through the support tube and the frame.
Figure 2:
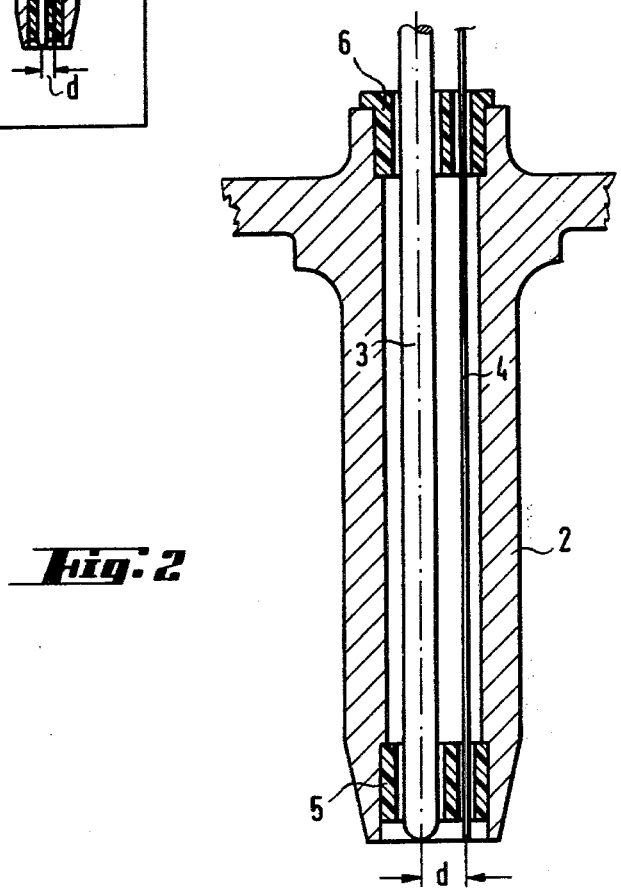
FIG. 2 is an enlargement of a part of FIG. 1.

The section illustrated in FIG. 1 shows the support frame 1, to which support frame the support tube 2 is rigidly connected. The ram 3 and the sensor 4 are arranged axially parallel inside the support tube 2. As FIG. 2 illustrates, in which the support tube is illustrated enlarged with respect to the scale of FIG. 1, the ram 3 and the sensor 4 are held in the continuous uniform or constant spacing d by means of the guide pieces 5 and 6. These pieces are made advantageously of a material with good slide characteristics e.g., a suitable synthetic material or plastic. In this manner the axial vibrations or oscillations of the ram 3 are prevented from being transmitted by frictional forces to the guide pieces 5 and 6 and from these to the sensor 4.

The transmitter for the mechanical oscillations comprises the electromotor 7 which can be controlled in its rotational speed and the device 8 which is coupled with the electromotor, e.g., a crank gear or mechanism or an eccentric arrangement, by the aid of which the rotational movement of the electromotor 7 is converted into a back and forth translational movement and is transmitted to the ram 3.

The transmitter for the mechanical oscillations of variable frequency, which transmitter comprises the electromotor 7 and the device 8 for the conversion of the rotational movement into a back and forth movement, is accommodated in a frame 9. The frame 9 is mounted in the support frame 1 held by resilient blocks or pads 10 such that no oscillations of the transmitter can influence or act on the support frame and from this act on the oscillation pickup 11, the latter also being fastened to the support frame.

In the embodiment example, this oscillation pickup comprises a piezoelectric operating mechanical-electrical transducer. The transducer is connected with the connection bolt 13 in an electrically conductive manner by means of a spring 12, the bolt 13 being fastened onto the frame 1 by means of the insulation member 14. On the other hand the oscillation pickup or receiver 11 is connected with the sensor 4, which sensor passes on the mechanical oscillations which are sensed with its other end to the oscillator pickup.

The resilient suspension protects the oscillation pickup from destruction with improper loading of the sensor 4. The ram 3 is also connected with an oscillation pickup 29. The output voltage of the latter, which corresponds to the vibration of the ram 3, represents the transmitter for the frequency of the mechanical oscillations. The output voltages of both oscillation pickups are placed in the electronic device 30, for example via amplifiers A, the electronic device 30 also being accommodated in the support frame 1. The output signals of the electronic unit 30 are fed to the multiple plug-in connection 31 via lines 30a, from which plug-in connection the output signals are supplied to a two coordinate writer instrument W. The operating voltages for the electronic unit 30 as well as for the electromotor 7 are fed to the electronic unit and electromotor via the multiple plug-in connection.

If the oscillations of the ram 3, as shown by the example illustrated in FIG. 3, are transmitted by placement of the supprt tube 2 on a body part 15, oscillateable organs which are located in the range of the oscillations which are transmitted to the body part 15, e.g., the arteries 16, are excited into oscillations. These oscillations are sensed by the sensor 4 on the surface of the body part 15. The amplitude of these oscillations reach a maximum when the frequency of the transmitter corresponds with the characteristic frequency of the oscilateable organ.

In the manner that the ram 3 and the sensor 4 have a defined and constant spacing, the reproducability of the measurements with respect to the known devices is considerably improved. A further improvement according to a further formation of the invention is attained in that means are provided for the adjustment of the pressure by which the support tube is placed on the body.

As FIG. 3 shows, adjustment of the application pressure can be done by means of the moving weight, which moving weight is displaceable on one of the arms of the scale or balance beam 18, the latter carrying on its other arm a reception device 19 for the support frame 1. The balance beam 18 is carried by a bearing 20, which bearing is fastened on a stand. After the moving weight has first been adjusted such that the weight has equalized or adjusted the other arm up to the desired application pressure, the height of the bearing 20 is adjusted on the stand 21, such that the balance beam 18 lies horizontally when the support tube 2 is set on the body part 15. For achieving satisfactory measurements, the body and the body part, respectively, in which the organ is located, the characteristic frequency of which is to be determined, are set or positioned completely quietly at rest. This can be achieved e.g. by supporting the body part in a bed 22 which is individually adjusted to the form of the body part.

The arrangement illustrated in FIG. 3 is not only suited for measurements during which the support tube 2 is set on the body from above, but it even permits measurements during which the support tube 2 is applied to the body from below. For this it suffices to insert the support frame 1 into the receiver device 19 such that the support tube 2 points upwardly and to adjust the moving weight 17 such that the weight on the other arm of the balance beam 18, instead of being undercompensated by the amount of of the desired application pressure, is now overcompensated by the same amount.

FIG. 4 shows the plan view of an arrangement for the adjustment of the application pressure with a horziontally directed support tube. The balance beam 18 for this purpose is rotatably mounted about the vertical axle 23 in the holding piece 24, which holding piece 24 is attached on the stand 21. Between the adjustment arm 23 which is located on the holding piece 24 and the balance beam 18, the spring scale 26 is tensioned, by which spring scale the application pressure of the support tube 2 on the body 27 can be measured. Under circumstances when necessary the application pressure is to be adjusted to the desired value by means of the adjustment nut 28.

While we have disclosed several embodiments of the present invention, it is to be understood that these embodiments are given by example only and not in a limiting sense.

We claim:

1. A device including a transmitter for mechanical oscillations of variable frequency and an oscillation pickup for determination of the mechanical characteristic frequency of blood vessels, tendons, bones or similar organs in a body, whereby these organs act as coupling members between the transmitter and the oscillation pickup, comprising a support frame, a common support tube having one end of the support tube being rigidly connected with said support frame, a transmitter mounted in said support frame, an oscillation pickup mounted in said support frame mutually decoupled from said transmitter, transmission means operatively connected from said transmitter to the body, and from the body to said oscillation pickup, respectively, said transmission means being mounted inside of said common support tube, said common support tube having another end adapted to be set on the body.

2. The device according to claim 1, further comprising means for adjustment of application pressure with which said support tube is set on the body.

3. The device according to claim 2, wherein said adjustment means comprises, a two-arm balance beam, bearing means for operatively supporting said balance beam, said support frame is suspended on said balance beam on one arm thereof, a moveable weight adjustably mounted on the other arm of said balance beam, whereby the application pressure of the support tube is adjustable by means of the moveable weight on said balance beam.

4. The device according to claim 1, wherein said transmitter includes a continuous action controllable electromotor, said transmission means includes a ram, means for converting the rotational movement of said electromotor into a back and forth translational movement and for transmitting the latter to said ram.

5. The device according to claim 1, wherein said transmission means includes a sensor, said oscillation pickup comprises a mechanical-electrical transducer, said transducer is resiliently clamped in said support frame, said transducer is connected to said sensor, whereby the oscillations which are picked up by said sensor on the surface of the body are transmitted to said transducer.

6. The device according to claim 1, further comprising a two coordinate writing means for drawing the output voltage of said oscillation pickup as a function of the frequency of said transmitter.

7. The device according to claim 1, wherein said transmission means comprises, a ram operatively connected to said transmitter, and a sensor operatively connected to said oscillation pickup.

8. The device according to claim 7, further comprising means for mounting said sensor and said ram in said support tube in axially parallel arrangement at constant spacing from each other, said mounting means for permitting said transmission means to longitudinally slide relative thereto with low friction.

9. The device according to claim 1, further comprising amplifier means connected to said oscillation pickup.

* * * * *